United States Patent [19]

Pall et al.

[11] Patent Number: 5,100,564
[45] Date of Patent: Mar. 31, 1992

[54] BLOOD COLLECTION AND PROCESSING SYSTEM

[75] Inventors: David B. Pall; Thomas C. Gsell, Glen Cove, both of N.Y.

[73] Assignee: Pall Corporation, Glen Cove, N.Y.

[21] Appl. No.: 609,654

[22] Filed: Nov. 6, 1990

[51] Int. Cl.$^5$ .................... B01D 21/26; B01D 39/16; B04B 15/00

[52] U.S. Cl. .................... 210/782; 210/767; 210/806; 210/295; 210/323.1; 210/360.1; 210/380.1; 210/435; 210/496; 210/514

[58] Field of Search ............ 210/94, 257.1, 295, 210/314, 323.1, 360.1, 380.1, 348, 435, 496, 513, 514, 767, 782, 787, 789, 806; 604/6, 406, 4, 5; 494/20, 21, 32, 33, 37

[56] References Cited

U.S. PATENT DOCUMENTS

| | | | |
|---|---|---|---|
| 4,111,199 | 9/1978 | Djerassi | 604/6 |
| 4,330,410 | 5/1982 | Takenaka et al. | 210/767 |
| 4,416,777 | 11/1983 | Kuroda et al. | 210/446 |
| 4,447,220 | 5/1984 | Eberle | 494/26 |
| 4,543,084 | 9/1985 | Bailey | 494/20 |
| 4,596,657 | 6/1986 | Wisdom | 210/206 |
| 4,675,117 | 6/1987 | Neumann et al. | 210/789 |
| 4,680,025 | 7/1987 | Kruger et al. | 604/6 |
| 4,714,457 | 12/1987 | Alterbaum | 494/20 |
| 4,753,739 | 6/1988 | Noble | 210/787 |
| 4,767,541 | 8/1988 | Wisdom | 210/749 |
| 4,810,378 | 3/1989 | Carmen et al. | 210/206 |
| 4,855,063 | 8/1989 | Carmen et al. | 210/749 |
| 4,880,548 | 11/1989 | Pall et al. | 210/767 |
| 4,892,668 | 1/1990 | Harmony et al. | 210/782 |
| 4,909,949 | 3/1990 | Harmony et al. | 210/513 |
| 4,915,848 | 4/1990 | Carmen et al. | 210/749 |
| 4,919,823 | 4/1990 | Wisdom | 210/749 |
| 4,923,620 | 5/1990 | Pall | 210/767 |
| 4,925,572 | 5/1990 | Pall | 210/767 |
| 4,943,287 | 7/1990 | Carmen | 604/408 |
| 4,985,153 | 1/1991 | Kuroda et al. | 210/782 |
| 4,997,577 | 3/1991 | Stewart | 210/767 |

FOREIGN PATENT DOCUMENTS

0267286 5/1988 European Pat. Off. .

Primary Examiner—W. Gary Jones
Attorney, Agent, or Firm—Leydig, Voit & Mayer

[57] ABSTRACT

A system for collecting and processing donated blood comprises a first porous medium interposed between a blood collection bag and a satellite bag and a second porous medium interposed between the blood collection bag and another satellite bag. The porous media are leucocyte depletion media. The system can be used to centrifuge whole blood into one or more components, and a means for protecting the system during centrifugation including a bracket carried by the centrifuge bucket for receiving the porous media.

123 Claims, 2 Drawing Sheets

BLOOD COLLECTION AND PROCESSING SYSTEM

TECHNICAL FIELD

This invention relates to a system for processing blood donated for the purpose of therapeutic transfusion of blood components and, particularly, to improved methods and apparatuses for preparing, from the donated whole blood, platelet-rich plasma (hereinafter PRP), packed red cells (hereinafter PRC), platelet concentrate (hereinafter PC), and plasma.

BACKGROUND OF THE INVENTION

The development of plastic blood collection bags facilitated the separation of donated whole blood into its various components, thereby making platelet concentrates available as a transfusion product. The separation of a single unit of donated whole blood, about 450 milliliter in USA practice, into its components is typically accomplished by use of differential sedimentation.

A typical procedure used in the United States, the citrate-phosphate-dextrose-adenine (CPDA-1) system, utilizes a series of steps to separate donated blood into three components, each component having substantial therapeutic and monetary value. The procedure typically utilizes a blood collection bag which is integrally attached via flexible tubing to at least one, and preferably two or more, satellite bags. Whole blood may be thus collected and processed as follows:

(1) The donated whole blood is collected from the donor's vein directly into the blood collection bag which contains the nutrient and anti-coagulant containing CPDA-1.

(2) The blood collection bag is centrifuged together with its satellite bags, thereby concentrating the red cells as packed red cells (PRC) in the lower portion of the blood collection bag and leaving in the upper portion of the bag a suspension of platelets in clear plasma, which is known as platelet-rich plasma (PRP).

(3) The blood collection bag is transferred, with care not to disturb the interface between the supernatant PRP layer and the sedimented PRC layer, into a device known as a "plasma extractor" which comprises an opaque back plate and a transparent front plate; the two plates are hinged together at their lower ends and spring biased toward each other such that a pressure of about 90 millimeters of mercury is developed within the bag.

With the blood collection bag positioned between the two plates, a valve or seal in the flexible tubing is opened allowing the supernatant PRP to flow into a first satellite bag. As the PRP flows out of the blood collection bag, the interface with the PRC rises. The operator closely observes the position of the interface as it rises and clamps off the connecting tube when in his judgment as much PRP has been transferred as is possible, consistent with allowing no red cells to enter the first satellite bag. This is a time consuming operation during which the operator must visually monitor the bag and judiciously and arbitrarily ascertain when to shut-off the connecting tube.

The blood collection bag, now containing only PRC, may be detached and stored at 4° C. until required for transfusion into a patient, or a valve or seal in the tubing may be opened so that the PRC may be transferred to a satellite bag using either the pressure generated by the plasma extractor apparatus, or by placing the blood collection apparatus in a pressure cuff, or by elevation to obtain gravity flow.

(4) The PRP-containing satellite bag, together with another satellite bag, is then removed from the extractor and centrifuged at an elevated G force with the time and speed adjusted so as to concentrate the platelets into the lower portion of the PRP bag. When centrifugation is complete, the PRP bag contains sedimented platelets in its lower portion and clear plasma in its upper portion.

(5) The PRP bag is then placed in the plasma extractor, and most of the clear plasma is expressed into a satellite bag, leaving the PRP bag containing only sedimented platelets in about 50 ml of plasma; in a subsequent step, this platelet composition is dispersed to make platelet concentrate (PC). The PRP bag, now containing a PC product, is then detached and stored for up to five days at 20°-22° C., until needed for a transfusion of platelets. For use with adult patients, the platelets from 6-10 donors are, when required, pooled into a single platelet transfusion.

(6) The plasma in the satellite bag may itself be transfused into a patient, or it may be separated by complex processes into a variety of valuable products.

Commonly used systems other than CPDA-1 include Adsol, Nutricell, and SAG-M. In these latter systems, the collection bag contains only anti-coagulant, and the nutrient solution may be preplaced in a satellite bag. This nutrient solution is transferred into the PRC after the PRP has been separated from the PRC, thereby achieving a higher yield of plasma and longer storage life for the PRC.

With the passage of time and accumulation of research and clinical data, transfusion practices have changed greatly. One aspect of current practice is that whole blood is rarely administered; rather, patients needing red blood cells are given packed red cells, patients needing platelets are given platelet concentrate, and patients needing plasma are given plasma.

For this reason, the separation of blood into components has substantial therapeutic and monetary value. This is nowhere more evident than in treating the increased damage to a patient's immune system caused by the higher doses and stronger drugs now used during chemotherapy for cancer patients. These more aggressive chemotherapy protocols are directly implicated in the reduction of the platelet content of the blood to abnormally low levels; associated internal and external bleeding additionally requires more frequent transfusions of PC, and this has caused platelets to be in short supply and has put pressure on blood banks to increase platelet yield per unit of blood.

Blood bank personnel have responded to the increased need for blood components by attempting to increase PRC and PC yield in a variety of ways, including attempting to express more PRP prior to stopping flow from the blood collection bag. This has often proved to be counterproductive in that the PRP, and the PC subsequently extracted from it, are not infrequently contaminated by red cells, giving a pink or red color to the normally light yellow PC. The presence of red cells in PC is so highly undesirable that pink or red PC is frequently discarded, or subjected to recentrifugation, both of which increase operating costs.

The devices and methods of this invention alleviate the above-described problems and, in addition, provide a higher yield of superior quality PRC and PC.

In addition to the three above-listed components, whole blood contains white blood cells (known collectively as leucocytes) of various types, of which the most important are granulocytes and lymphocytes. White blood cells provide protection against bacterial and viral infection.

The transfusion of blood components which have not been leuco-depleted is not without risk to the patient receiving the transfusion. Some of these risks are detailed in U.S. Pat. No. 4,923,620, incorporated herein by reference, and in U.S. Pat. No. 4,880,548, also incorporated herein by reference.

In the above described centrifugal method for separating blood into the three basic fractions, the leucocytes are present in substantial quantities in both the packed red cells and platelet-rich plasma fractions. It is now generally accepted that it would be highly desirable to reduce the leucocyte concentration of these blood components to as low a level as possible. While there is no firm criterion, it is generally accepted that many of the undesirable effects of transfusion would be reduced if the leucocyte content were reduced by a factor of about 100 or more prior to administration to the patient. This approximates reducing the average total content of leucocytes in a single unit of PRC or PRP to less than about $1 \times 10^7$, and in a unit of PRP or PC to less than about $1 \times 10^6$. Devices which have previously been developed in attempts to meet this objective have been based on the use of packed fibers, and have generally been referred to as filters. However, it would appear that processes utilizing filtration based on separation by size cannot succeed for two reasons. First, leucocytes can be larger than about 15 μm (e.g., granulocytes and macrocytes) to as small as 5 to 7 μm (e.g., lymphocytes). Together, granulocytes and lymphocytes represent the major proportion of all of the leucocytes in normal blood. Red blood cells are about 7 μm in diameter, i.e., they are about the same size as lymphocytes, one of the two major classes of leucocytes which must be removed. Secondly, all of these cells deform so that they are able to pass through much smaller openings than their normal size. Accordingly, it has been widely accepted that removal of leucocytes is accomplished mainly by adsorption on the internal surfaces of porous media, rather than by filtration.

The separation of the various blood components using centrifugation is attended by a number of problems. First, in the separation of platelet-rich plasma from PRC, e.g., step 3 above, it is difficult to efficiently obtain the maximum yield of platelets while preventing red cells from entering the plasma. Secondly, when PRP is centrifuged to obtain a layer consisting principally of platelets concentrated at the bottom of the PRP-containing bag, e.g., step 4 above, the platelets so concentrated tend to form a dense aggregate which must be dispersed in plasma to form platelet concentrate. The dispersion step is usually carried out by gentle mixing, for example, by placing the bag on a moving table which rotates with a precessing tilted motion. This mixing requires several hours, a potentially undesirable delay, and is believed by many researchers to result in a partially aggregated platelet concentrate. It is further believed that the platelets may be damaged by the forces applied during centrifugation.

An ideal device for the leucocyte depletion of PRC or PRP would be inexpensive, relatively small, and be capable of rapidly processing blood components obtained from about one unit or more of donated whole blood in, for example, less than about one hour. Ideally, this device would also reduce the leucocyte content to the lowest possible level, while avoiding the problems described above.

Because of the high cost and limited availability of red blood cells, a device comprising a porous medium used to deplete leucocytes from PRC should deliver the highest possible proportion of the red cells present in the donated blood. In accordance with the invention, it may also be preferable that the PRC porous medium be capable of removing platelets, as well as fibrinogen, fibrin strands, tiny fat globules, and other components such as microaggregates which may be present in whole blood.

If the leucocyte depletion device comprises a porous structure, microaggregates, gels, fibrin, fibrinogen and fat globules tend to collect on or within the pores, causing blockage which inhibits flow. Conventional processes, in which the filter for depleting leucocytes from PRC is pre-conditioned by passing saline through the filter assembly with or without a post-filtration saline flush, are undesirable because the liquid content of the transfusion is unduly increased, thus potentially overloading the patient's circulatory system with liquid. An objective of an embodiment of this invention is a leucocyte depletion device which removes leucocytes and these other elements with high efficiency and without clogging, requires no preconditioning prior to processing PRC derived from freshly drawn blood, and does not require post-filtration flushing to reclaim red cells remaining in the filter.

Platelet preparations contain varying amounts of leucocytes. Platelet concentrates prepared by the differential centrifugation of blood components will have varying levels of leucocyte contamination related to the time and to the magnitude of the force developed during centrifugation. It has been demonstrated that leucocyte removal efficiencies of 81 to 85% are sufficient to reduce the incidence of febrile reactions to platelet transfusions. Several other recent studies report a reduction in alloimmunization and platelet refractoriness at levels of leucocyte contamination $<1 \times 10^7$ per unit. The level of leucocyte contamination in unfiltered conventional platelet preparations of 6 to 10 pooled units is generally at a level of about $5 \times 10^8$ or greater. For a single unit of PC averaging a leucocyte contamination level (under current practice) of about $7 \times 10^7$ leucocytes, the goal after filtration is less than $1 \times 10^6$ leucocytes. The existing studies, therefore, suggest the desirability of at least a two log (99%) reduction of leucocyte contamination. More recent studies suggest that a three log (99.9%) or even a four log (99.99%) reduction would be significantly more beneficial.

An additional desirable criterion is to restrict platelet loss to about 15% or less of the original platelet concentration. Platelets are notorious for being "sticky", an expression reflecting the tendency of platelets suspended in blood plasma to adhere to any non-physiological surface to which they are exposed. Under many circumstances, they also adhere strongly to each other.

In any system which depends upon filtration to remove leucocytes from a platelet suspension, there will be substantial contact between platelets and the internal surfaces of the filter assembly. The filter assembly must be such that the platelets have minimal adhesion to, and are not significantly adversely affected by contact with, the filter assembly's internal surfaces. Such a filter assembly is an objective of this invention.

SUMMARY OF THE INVENTION

In the devices and methods of this invention, leucocyte depletion is carried out at the time the blood is processed, which in USA practice is generally within 6-8 hours of the time the blood is drawn. Thus, as a blood product is transferred from the bag in which it is contained, leucocytes are removed by the appropriate porous medium and leucocyte-depleted blood product is collected in the appropriate satellite bag. In accordance with the invention, a system is provided whereby PRP is leucocyte depleted by interposing between the blood collection bag and a first satellite bag at least one porous medium for depleting leucocytes from PRP; PRC is leucocyte depleted by interposing between the blood collection bag and a second satellite bag at least one porous medium for removing leucocytes from PRC. The invention also comprises a centrifugation system wherein one (or both) of the interposed leucocyte depletion filter assemblies is (are) cooperatively arranged with a centrifuge bucket in a manner such that the filter assembly, the porous medium in the filter assembly, and the blood bags are not damaged by the very large forces generated during the centrifugation process.

DESCRIPTION OF THE PREFERRED EMBODIMENTS

The present invention involves a blood collection and processing assembly comprising a first container and a second container, and a conduit interconnecting the first container with the second container; and at least one third container and a conduit interconnecting the first container with the third container; and having interposed between the first container and a second container, at least one first porous medium; and having interposed between the first container and a third container, at least one second porous medium. The first porous medium may be a leucocyte depletion medium, a red cell barrier medium, an assembly comprising a leucocyte depletion medium and a red cell barrier medium, or combinations thereof. The second porous medium may be a leucocyte depletion medium which may, optionally, include a microaggregate filter element and/or a gel pre-filter element. In a preferred embodiment, the invention also includes a bracket which secures the filter assembly or one or more components of an assembly in place during centrifugation so that it (they) is (are) not damaged by the stresses generated during centrifugation.

In another embodiment of the invention, the blood collection and processing assembly comprises first and second containers interconnected with a conduit, and a porous medium for depleting leucocytes from PRC wherein the porous medium has a CWST greater than about 53 dynes/cm.

Figure 1:
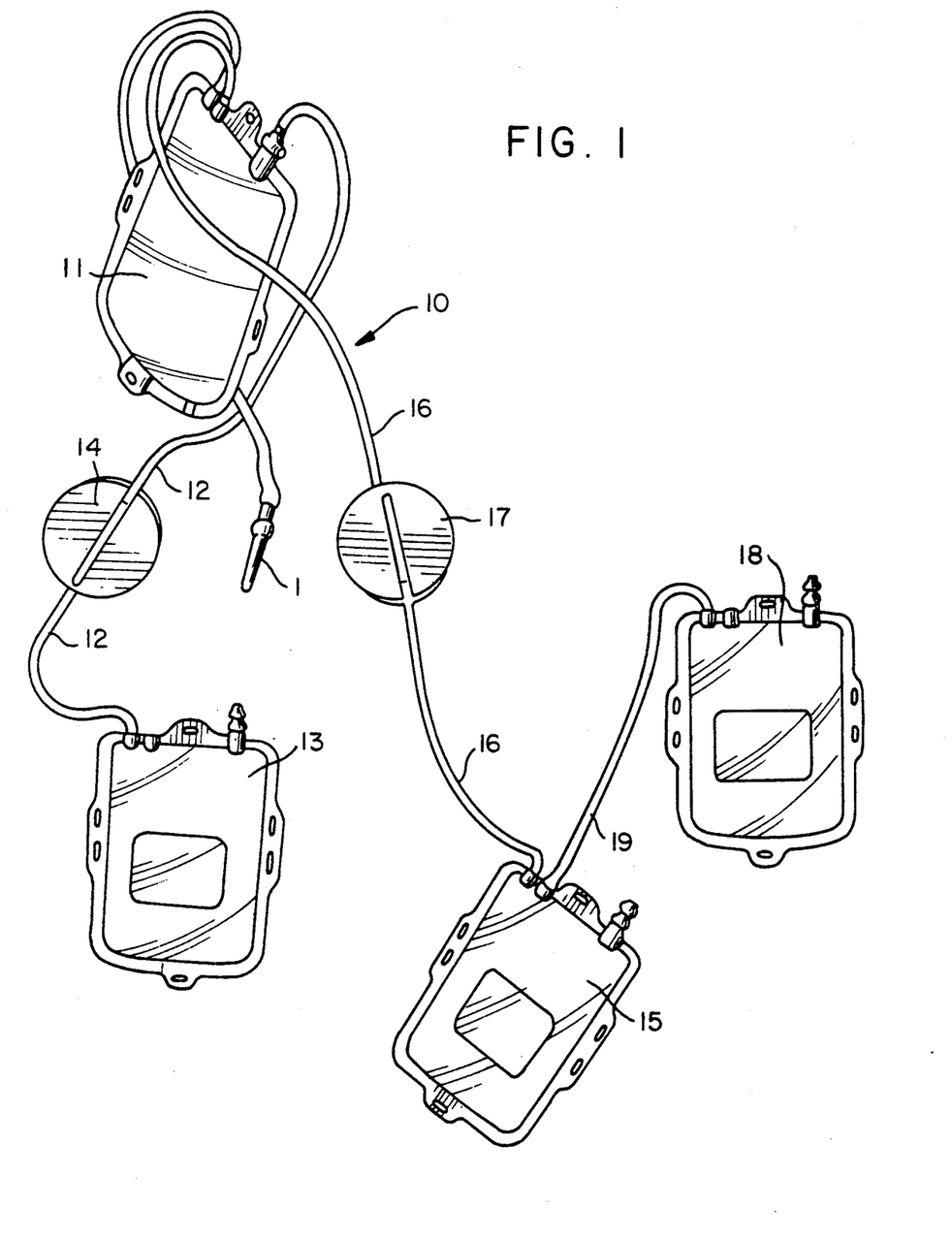
FIG. 1 is an embodiment of a blood set according to the invention.
Figure 2:
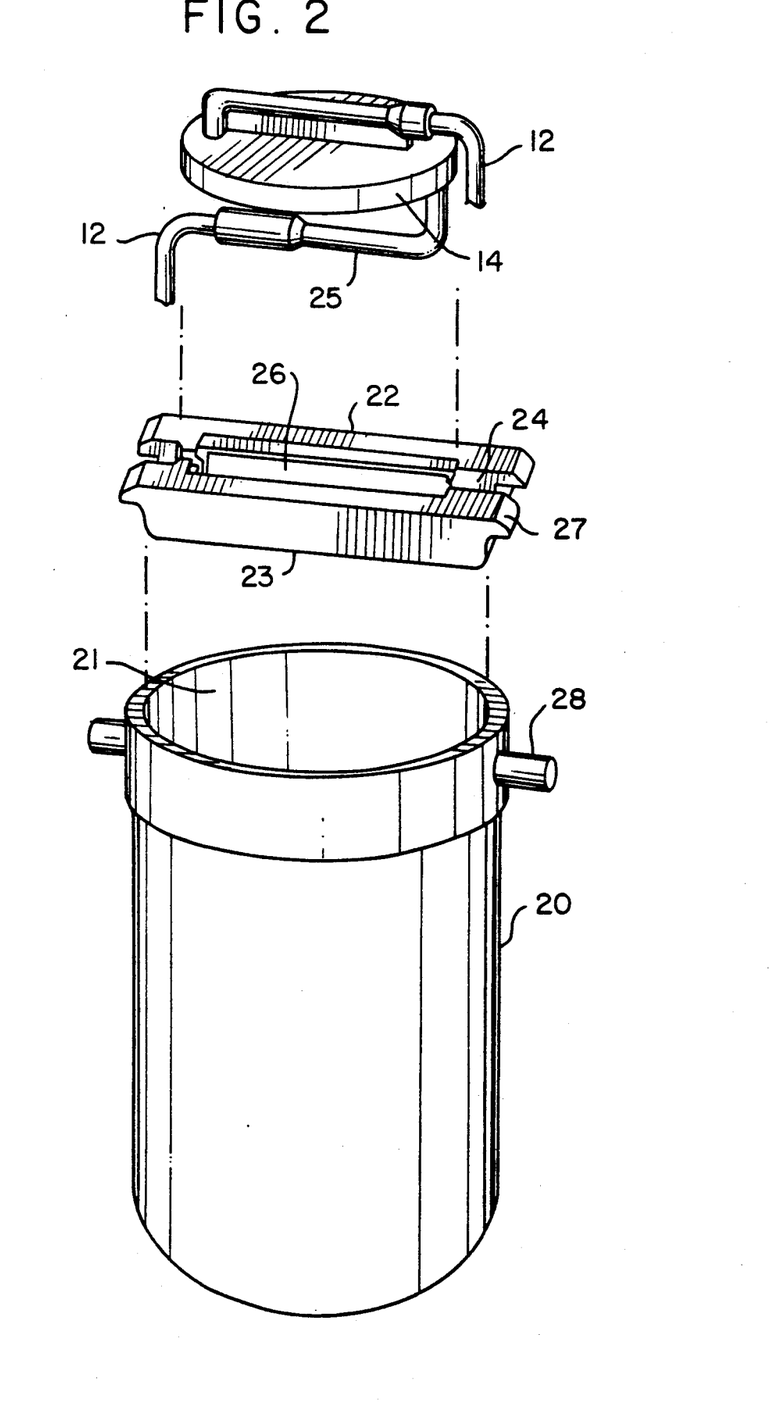
FIG. 2 is an exploded perspective view of one embodiment of a filter assembly, a centrifuge bucket, and a holder to properly position the filter assembly on the bucket.

An embodiment of the invention will be better understood by reference to FIGS. 1 and 2.

FIG. 1 shows a blood collection and processing system of the invention, generally denoted as 10. The blood collection set 10 comprises a first container or blood collection bag 11, a needle or cannula 1 adapted to be inserted into the donor, tubing 16, preferably flexible tubing, connecting the blood collection bag 11 and a second container (first satellite bag) 15 for PRP, and a filter assembly 17 in the tubing 16 interposed between the collection bag 11 and the first satellite bag 15. Collection bag 11 is also connected via tubing 12, preferably flexible tubing, to a third container (second satellite bag) 13 for PRC; a filter assembly 14 in the tubing 12 is interposed between the collection bag 11 and the second satellite bag 13. In another embodiment of the invention, the blood collection and processing assembly 10 may also include an additional (third) satellite bag 18 for PC connected to the first satellite bag 15 via tubing 19, preferably flexible tubing. A seal, valve, or transfer leg closure or cannula (not illustrated) may also be positioned in the flexible tubing 12, 16, and/or 19; this seal (or seals) is broken or opened when fluid is to be transferred between bags.

The blood collection and processing assembly 10, with one or more satellite bags attached or connected via a conduit, may be used integrally to separate components from whole blood. During the centrifugation step in which the red cells are concentrated at the bottom of collection bag 11, forces of up to about 5000 times gravity (5000G) or more may be generated. Therefore, collection bag 11 is preferably flexible, as are the other bags, allowing them to settle to the bottom and against the walls of a centrifuge bucket 20, so that the bags themselves are subject to little or no stress.

In contrast to the flexibility and pliability of the bags and tubing, the porous medium is typically contained in a rigid plastic housing (the combination of which is termed a filter assembly). The PRC housing is typically of larger dimensions than the PRP housing, and is therefore subject to an increased probability of suffering or causing damage during centrifugation. For example, a typical PRC filter assembly may weigh about 20 grams (about 0.04 lbs), but its effective weight may be 5000 times greater, or about 200 lbs, under centrifugation conditions of 5000G. In conventional centrifugation systems it is therefore difficult to avoid shattering the plastic housing. Even careful placement of the PRC filter in the centrifuge bucket is likely to result in damage to the plastic tubing or to the bags. Furthermore, it is undesirable to enlarge the centrifuge bucket to accommodate the filter in the bucket during the centrifugation step, as this would not only require the use of a larger and more costly centrifuge, but it would also require retraining the thousands of blood processing technicians to expertly assemble the blood bag sets into a new type of centrifuge bucket. Accordingly, it is desirable that an improved blood collection and processing system or set should be usable with existing centrifuge buckets. In accordance with the invention, this is preferably accomplished by locating the PRC filter assembly away from the greatest amount of G force; this is more preferably outside or partly outside of the conventionally used centrifuge bucket, in the manner shown in FIG. 2.

In FIG. 2 the bucket 20 depicts a centrifuge bucket such as is used in current blood bank practice. These buckets are typically constructed with heavy walls of high strength steel which enclose open space 21 into which the blood bag, its satellite bags, and the interposed tubing may be placed. The bracket 22 used to hold a filter assembly may be made of any high strength material, preferably metal or metallic alloy; titanium or stainless steel are more preferred for their strength and the ease with which sanitary conditions can be maintained. The lower portion 23 of bracket 22 is configured to cooperatively fit into cavity 21, preferably at a depth of about 0.5 to about 1 cm. Spring clips or other means may be used to position and/or retain bracket 22 in the bucket 20. Groove 24 located in the upper portion of bracket 22, is preferably configured to cooperatively accept the outlet port 25 of the filter assembly 14, and to allow the bottom portion of the filter assembly 14 to rest on the flat upper surfaces of bracket 22 adjacent to groove 24. The central portion 26 of groove 24 may be proportioned such that port 25 of the filter assembly 14 fits into at least a portion of the groove 24 with a friction fit. The ends of groove 24 are preferably reduced to a width such that flexible tubing 12 connected to the inlet and outlet of the filter assembly 14 is firmly retained, thereby helping to stabilize the filter assembly 14 when positioned onto bracket 22. The unsupported portions of flexible tubing 12 then drop into the bucket in communication with the balance of the blood collection set contained therein. It is preferred that the bracket 22 retain the filter assembly 14 so that the plane of the porous medium is substantially perpendicular to the G force created during operation of the centrifuge. Also, the bracket and filter assembly should be positioned on or in the centrifuge bucket without interfering with the normal free-swinging action of the bucket 20 in the centrifuge during rotation.

Because the PRP filter is typically relatively small and very light, it may be positioned within the bucket with the bags and the tubing. In another embodiment of the invention, however, the groove 24 may be configured to hold more than one filter assembly, for example, both a PRC and a PRP assembly.

In another embodiment of the invention, a larger bracket may be employed to hold a first filter assembly and a second bracket holding a second filter assembly may be nested on top of the first bracket and filter assembly. One skilled in the art will recognize that various designs, configurations, and/or means may be employed to accomplish these functions.

Definitions

The following definitions are used in reference to the invention:

A) Blood Product: anti-coagulated whole blood (AWB); packed red cells obtained from AWB; platelet-rich plasma (PRP) obtained from AWB; platelet concentrate (PC) obtained from AWB or PRP; plasma obtained from AWB or PRP; red cells separated from plasma and resuspended in physiological fluid; and platelets separated from plasma and resuspended in physiological fluid. As used herein, blood component or product refers to the components described above, and to similar blood products obtained by other means and with similar properties. In accordance with the invention, each of these blood products is processed in the manner described herein.

B) Unit of Whole Blood: blood banks in the United States commonly draw about 450 milliliters (ml) of blood from the donor into a bag which contains an anticoagulant to prevent the blood from clotting. However, the amount drawn differs from patient to patient and donation to donation. Herein the quantity drawn during such a donation is defined as a unit of whole blood.

C) Unit of Packed Red Cells (PRC), Platelet-rich Plasma (PRP), or Platelet Concentrate (PC): As used herein, a "unit" is defined by the United States' practice, and a unit of PRC, PRP, PC, or of red cells or platelets in physiological fluid or plasma, is the quantity derived from one unit of whole blood. Typically, the volume of a unit varies. For example, the volume of a unit of PRC varies considerably dependent on the hematocrit (percent by volume of red cells) of the drawn whole blood, which is usually in the range of about 37% to about 54%. The concomitant hematocrit of PRC, which varies over the range from about 50 to over 80%, depends in part on whether the yield of one or another blood product is to be minimized. Most PRC units are in the range of about 170 to about 350 ml, but variation below and above these figures is not uncommon.

D) Porous medium: refers to the porous medium through which one or more blood components pass. The PRC porous medium depletes leucocytes from the packed red cell component. The platelet or PRP porous medium refers generically to any one of the media which deplete leucocytes from the non-PRC blood components, i.e., from PRP or from PC. The red cell barrier medium blocks the passage of red cells and depletes leucocytes from PRP to a greater or lesser degree while allowing the passage of platelets.

As noted in more detail below, the porous medium for use with PRC may be formed from any natural or synthetic fiber (or from other materials of similar surface area and pore size) compatible with blood. Preferably, the critical wetting surface tension (CWST) of the porous medium is within a certain range, as noted below and as dictated by its intended use. The pore surfaces of the medium may be modified or treated in order to achieve the desired CWST. For example, the CWST of a PRC porous medium is typically above about 53 dynes/cm.

The porous medium for use with PRP may be formed from any natural or synthetic fiber or other porous material compatible with blood. Preferably, the CWST and zeta potential of the porous medium are within certain ranges, as disclosed below and as dictated by its intended use. For example, the CWST of a PRP porous medium is typically above about 70 dynes/cm.

The porous media according to the invention may be connected to a conduit interposed between the containers, and may be positioned in a housing which in turn can be connected to the conduit. As used herein, filter assembly refers to the porous medium positioned in a suitable housing. Preferably, the porous medium forms an interference fit at its edges when assembled into the housing.

The porous medium may be configured as a flat sheet, a corrugated sheet, a web, or a membrane, although it is not intended that the invention should be limited thereby.

E) Voids volume is the total volume of all of the pores within a porous medium. Voids volume is expressed hereinafter as a percentage of the apparent volume of the porous medium.

F) Critical Wetting Surface Tension: As disclosed in U.S. Pat. No. 4,880,548, the CWST of a porous medium may be determined by individually applying to its surface a series of liquids with surface tensions varying by 2 to 4 dynes/cm and observing the absorption or non-absorption of each liquid over time. The CWST of a porous medium, in units of dynes/cm, is defined as the mean value of the surface tension of the liquid which is absorbed and that of the liquid of neighboring surface tension which is not absorbed within a predetermined amount of time. The absorbed and non-absorbed values depend principally on the surface characteristics of the material from which the porous medium is made and secondarily on the pore size characteristics of the porous medium.

Liquids with surface tensions lower than the CWST of a porous medium will spontaneously wet the medium on contact and, if the pores of the medium are interconnected, liquid will flow through it readily. Liquids with surface tensions higher than the CWST of the porous medium may not flow at all at low differential pressures or may flow unevenly at sufficiently high differential pressures to force the liquid through the porous medium. In order to achieve adequate priming of a fibrous medium with a liquid such as blood, the fibrous medium preferably has a CWST in the range of about 53 dynes/cm or higher.

For the porous medium which is used to process PRC, it is preferred that the CWST be held within a range somewhat above the CWST of untreated polyester fiber (52 dynes/cm), for example, above about 53 dynes/cm and higher, and more preferably above about 60 dynes/cm. For the porous medium which is used to process PRP, it is preferred that the CWST be held within a range above about 70 dynes/cm.

The porous medium may be multi-layered and may be treated to modify the fiber surfaces, either before or after forming the fibrous lay-up. It is preferred to modify the fiber surfaces before forming the fibrous lay-up because a more cohesive, stronger product is obtained after hot compression to form an integral filter element.

G) Measurement of fiber surface area and of average fiber diameter: In accordance with the invention, a useful technique for the measurement of fiber surface area, for example by gas adsorption, is generally referred to as the "BET" measurement. The surface area of melt blown webs can be used to calculate average fiber diameter, using PBT as an example:

Total volume of fiber in 1 gram $= \frac{1}{1.38}$ cc (where 1.38 = fiber density of PBT, g/cc)

hence $\frac{\pi d^2 L}{4} = \frac{1}{1.38}$ (1)

Area of the fiber is $\pi d L = A_f$ (2)

Dividing (1) by (2), $\frac{d}{4} = \frac{1}{1.38 A_f}$ and $d = \frac{4}{1.38 A_f} = \frac{2.9}{A_f}$, or $(0.345 A_f)^{-1}$ where
 L = total length in cm of 1 gram of fiber,
 d = average fiber diameter in centimeters, and
 $A_f$ = fiber surface area in cm$^2$/g. If the units of d are micrometers, the units of $A_f$ become M$^2$/g (square meters/gram), which will be used hereinafter.

H) General procedure for measuring zeta potential: Zeta potential was measured using a sample cut from a ¼ inch thick stack of webs.

The zeta potential was measured by placing the sample in an acrylic filter holder which held the sample snugly between two platinum wire screens 100×100 mesh (i.e., 100 wires in each direction per inch). The meshes were connected, using copper wire, to the terminals of a Triplett Corporation model 3360 Volt-Ohm Meter, the mesh on the upstream side of the sample being connected to the positive terminal of the meter. A pH-buffered solution was flowed through the sample using a differential pressure of 45 inches of water column across the filter holder and the effluent was collected. For measurements at pH 7, a buffered solution was made by adding 6 ml pH 7 buffer (Fisher Scientific Co. catalog number SB108-500) and 5 ml pH 7.4 buffer (Fisher Scientific Co. catalog number SB110-500) to 1 liter pyrogen-free deionized water. For measurements at pH 9, a buffered solution was made by adding 6 ml pH 9 buffer (Fisher Scientific Co. catalog number SB114-500) and 2 ml pH 10 buffer (Fisher Scientific Co. catalog number SB116-500) to 1 liter pyrogen-free deionized water. The electrical potential across the filter holder was measured during flow (it required about 30 seconds of flow for the potential to stabilize) and was corrected for cell polarization by subtracting from it the electrical potential measured when flow was stopped. During the period of flow the pH of the liquid was measured using a Cole-Parmer model J-5994-10 pH meter fitted with an in-line model J-5993-90 pH probe. The conductivity of the liquid was measured using a Cole-Parmer model J-1481-60 conductivity meter fitted with a model J-1481-66 conductivity flow cell. Then the polarity of the volt meter was reversed, and the effluent was flowed backwards through the filter holder using a differential pressure of 45 inches of water column. As in the first instance the electrical potential measured during flow was corrected for cell polarization by subtracting from it the electrical potential measured after flow was stopped. The average of the two corrected potentials was taken as the streaming potential.

The zeta potential of the medium was derived from the streaming potential using the following relationship (J. T. Davis et al., *Interfacial Phenomena*, Academic Press, New York, 1963):

$$\text{Zeta Potential} = \frac{4\pi\eta}{DP} \cdot E_S \lambda$$

where $\eta$ is the viscosity of the flowing solution, D is its dielectric constant, $\lambda$ is its conductivity, $E_S$ is the streaming potential and P is the pressure drop across the sample during the period of flow. In these tests the quantity $4\pi\eta/DP$ was equal to 0.800.

In general, the donor's blood is received directly into the blood collection bag, which is connected to a satellite bag for PRP and a satellite bag for PRC. Preferably, the PRP satellite bag is in turn connected to a satellite bag for PC. As a blood component passes from one bag to the next, it passes through one of the porous media. Typically, as PRP passes from the collection bag, it may pass through one or more porous media—a leucocyte-depletion medium, a red cell barrier medium, a porous medium which combines the red cell barrier with leucocyte depletion in one porous medium, or a leucocyte depletion medium and a red cell barrier medium in series. As PRC passes from the collection bag to the PRC satellite bag, it may pass through at least one porous medium for use with PRC. One skilled in the art will recognize that the invention as described here may be reconfigured into different combinations. These different configurations and combinations are included within the scope of the invention.

In accordance with the invention, the blood collection and processing assembly should be able to withstand rigorous sterilization and centrifugation environments, typically consisting of radiation sterilization (at about 2.5 megarads), and/or autoclaving (at about 110° C. to about 120° C. for about 15 to 60 minutes), and/or centrifugation (typically about 2500-3500G for about 5 to 15 minutes; however, depending on which blood component product is intended to have maximum recovery, the centrifugation conditions may be as much as about 5,000G for 10-20 minutes).

Each of the components of the assembly will now be described in more detail below:

The containers which are used in the blood collection and processing assembly may be constructed of any material compatible with whole blood or blood components and capable of withstanding a centrifugation and sterilization environment. A wide variety of these containers are already known in the art. For example, blood collection and satellite bags are typically made from plasticized polyvinyl chloride, e.g. PVC plasticized with dioctylphthalate, diethylhexylphthalate, or trioctyltrimellitate. The bags may also be formed from polyolefin, polyurethane, polyester, and polycarbonate.

As used herein, the tubing may be any conduit or means which provides fluid communication between the containers, and is typically made from the same flexible material as is used for the containers, preferably plasticized PVC. A seal, valve, or transfer leg closure is typically located within the tubing. It is intended that the present invention is not limited by the type of material used to construct the containers or the conduit which connects the containers.

As noted above, donated whole blood is typically processed as soon as practicable in order to more effectively reduce or eliminate contaminating factors, including but not limited to leucocytes and microaggregates.

Leucocyte depletion has been heretofore typically performed during transfusion at bedside, however, in accordance with the subject invention leucocyte depletion is accomplished during the initial processing of the whole blood, which in United States practice is generally within 8 hours of collection from the donor. After the red cells have been sedimented by centrifuging, the supernatant PRP is expressed from the blood collection bag into a first satellite bag through one or more porous media which diminish the amount of leucocytes and/or block red cells, and the PRC remaining in the blood collection bag is then passed through a porous medium which removes leucocytes into a second satellite bag.

A preferred composition of the porous media is a mat or web composed of fibers, which are preferably thermoplastic. The fibers of the porous media may comprise any fiber compatible with blood, and may be either natural or synthetic fibers. The fibers used in the PRC porous medium preferably have a CWST above about 53 dynes/cm; for the platelet porous medium, above about 70 dynes/cm. In accordance with the invention, the fibers are preferably treated or modified in order to achieve or increase the CWST. For example, the fibers may be surface modified to increase the critical wetting surface tension (CWST) of the fibers. Also, the fibers may be bonded, fused, or otherwise fixed to one another, or they may be mechanically entwined. Other porous media, for example open cell foamed plastics, surface modified as noted above, may be similarly used.

While the porous media can be produced from any material compatible with blood, practical considerations dictate that consideration be given first to the use of commercially available materials. The porous media of this invention may be preferably formed, for example, from any synthetic polymer capable of forming fibers and of serving as a substrate for grafting. Preferably, the polymer should be capable of reacting with at least one ethylenically unsaturated monomer under the influence of ionizing radiation without the matrix being significantly or excessively adversely affected by the radiation. Suitable polymers for use as the substrate include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene fluoride, polyethylene, polypropylene, cellulose acetate, and Nylon 6 and 66. Preferred polymers are polyolefins, polyesters, and polyamides. The most preferred polymer is polybutylene terephthalate (PBT).

Surface characteristics of a fiber can be modified by a number of methods, for example, by chemical reaction including wet or dry oxidation, by coating the surface by depositing a polymer thereon, or by grafting reactions wherein the substrate or fiber surface is activated prior to or during wetting of the fiber surface by a monomer solution by exposure to an energy source such as heat, a Van der Graff generator, ultraviolet light, or to various other forms of radiation. A preferred method is a grafting reaction using gamma-radiation, for example, from a cobalt source.

An exemplary radiation grafting technique employs at least one of a variety of monomers each comprising an ethylene or acrylic moiety and a second group, which is preferred to be a hydrophilic group (e.g., —COOH, or —OH). Grafting of the fibrous medium may also be accomplished by compounds containing an ethylenically unsaturated group, such as an acrylic moiety, combined with a hydroxyl group, preferably monomers such as hydroxyethyl methacrylate (HEMA), or acrylic acid. The compounds containing an ethylenically unsaturated group may be combined with a second monomer such as methyl acrylate (MA), methyl methacrylate (MAA), or methacrylic acid. MA or MAA are preferably incorporated into the porous medium used to treat PRC, and methacrylic acid is preferably incorporated into the porous medium used to treat the PRP. Preferably, the methacrylic acid to HEMA monomer weight ratio in the modifying mixture may be between about 0.01:1 and about 0.5:1; preferably, the MA or MAA to HEMA monomer weight ratio in the modifying mixture may be between about 0.01:1 and about 0.4:1. Use of HEMA contributes to a very high CWST. Analogues with similar functional characteristics may also be used to modify the surface characteristics of fibers.

In a preferred embodiment of the invention, a porous medium for use with platelets typically comprises the type of device disclosed in U.S. Pat. No. 4,880,548, herein incorporated by reference.

In a first variation of the devices of this invention, the PRP derived from a single unit of about 450 cc of human blood is passed, typically during a flow interval of about 10 to 40 minutes, through a filter comprising grafted fibers, the element of the filter preferably comprising fibers with a surface area in the range of about 0.08 to about 1.0 square meters, and more preferably about 0.1 to about 0.7 square meters, with a voids volume in the range of about 50% to about 89%, and more preferably about 60% to about 85%. The filter element is preferably of right cylindrical form with the ratio of diameter to thickness preferably in the range of about 7:1 to about 40:1. The range of fiber diameter is preferred to be about 1.0 to about 4 $\mu$m and is more preferred to be in the range of about 2 to about 3 $\mu$m. These parameters can be varied; for example, the diameter of the filter element could be reduced and the thickness of the filter element increased while retaining the same total quantity of fiber, or the fibers could be larger in diameter while increasing the total quantity of fiber, or the fibers could be packed as opposed to preformed into a cylindrical disc. Such variations fall within the purview of this invention.

If desired, flow rate of the PRP through the filter can be regulated to obtain a total flow period of about 10 to 40 minutes by selecting the appropriate element diameter, element thickness, fiber diameter, and density, and/or by varying the diameter of tube 16 either upstream or downstream of the filter, or both up and downstream. At these flow rates, leucocyte depletion efficiency in excess of 99.9% may be achieved. These levels of efficiency result in a PC product with less than about $0.1 \times 10^6$ leucocytes per unit of PC compared with the target of less than about $1 \times 10^6$.

In a second variation of this invention, the interposed filter 17 is preferably made with smaller fiber surface area, smaller filter element flow area, higher filter element density, and reduced voids volume in relation to the first variation. The total quantity of fiber used is also reduced such that a preferred range for the fiber surface area of the filter element is about 0.04 to about 0.3 M$^2$ and a more preferred range is about 0.06 to about 0.20 M$^2$. A preferred range for the filter element flow area is about 3 to about 8 cm$^2$, and a more preferred range is about 4 to about 6 cm$^2$. A preferred range for the voids volume is about 71% to about 83%, and a more preferred range is from about 73% to about 80%. Because of its very small size, a preferred device in accordance with the second variation of the invention retains internally only about 0.5 to about 1 cc of PRP, representing less than a 0.5% loss of platelets.

Filters which are made in accordance with this second variation and which are interposed between the blood collection bag and PRP bag will generally remove about 85 to 99% or more of the incident leucocytes, a removal rate that is not sufficient to consistently achieve a residual leucocyte count of less than 10$^6$ leucocytes per unit of PC. A principal function of this device, however, is to act as an automatic "valve" during the decantation process by instantly stopping the flow of PRP at the moment that red cells contact the filter surface. The mechanism of this valve-like action is not well understood, but it may reflect aggregation of the red cells as they reach the filter surface, forming a barrier which prevents or blocks further flow of PRP through the filter element. Aggregation of red cells on contact with the filter surface appears to be related to the CWST and/or to other less well understood surface characteristics of the fibers which are generated by the herein described procedure for modifying the fibers. This theory for the proposed mechanism is supported by the existence of filters capable of highly efficient leucocyte depletion of human red blood cell suspensions and which have pore sizes as small as 0.5 $\mu$m, through which red cells pass freely and completely with no clogging, with applied pressure of the same magnitude as that used in the present invention. On the other hand, filters of the present invention, which typically have pore diameters larger than about 0.5 $\mu$m, abruptly stop the flow of red blood cells when the filter is contacted by the red cells. This suggests that the filter's valve-like action is not related to or caused by pore size or by a filtration mechanism. The mechanism of this valve-like action is not well understood, but it may reflect zeta potential-related aggregation of the red cells as they reach the filter surface, forming a barrier which prevents or blocks further flow of PRP through the filter element.

This second variation may also comprise a porous medium wherein the upstream portion of the medium is of a higher density than the downstream portion. For example, the porous medium may comprise a higher density upstream layer for blocking the passage of red blood cells and a lower density downstream layer for the depletion of leucocytes.

In a third variation of this invention, the fiber is surface modified in the same manner as in the preceding versions, but the fiber surface area of the element is increased while, at the same time, the density of the filter element is somewhat reduced. In this way, the automatic blockage of flow on contact by red cells is combined with very high efficiency of leucocyte depletion.

A preferred range of fiber surface area for the third variation of the invention is from about 0.3 to about 2.0 M$^2$, and a more preferred range is from about 0.35 to about 0.6 M$^2$. The upper limits of fiber surface area reflect the desire to accomplish the filtration in a relatively short time period, and may be increased if longer filtration times are acceptable. A preferred voids volume for a filter element is in the range of about 71% to about 83%, and more preferably about 75% to about 80%. A preferred filter element flow area is from about 2.5 to about 10 cm$^2$, and a more preferred area is from about 3 to about 6 cm$^2$. Leucocyte depletion efficiencies in excess of about 99.9%, which corresponds to an average residual leucocyte content per unit of less than about $0.05 \times 10^6$, can be obtained.

For all three of the above described variations of the porous medium for use with PRP, a preferred range for the CWST of the fiber is preferably above about 70 dynes/cm, typically about 70 to 115 dynes/cm; a more preferred range is 90 to 100 dynes/cm, and a still more preferred range is 93 to 97 dynes/cm. A preferred range for the zeta potential (at the pH of plasma (7.3)) is about $-3$ to about $-30$ millivolts, a more preferred range is about $-7$ to about $-20$ millivolts, and a still more preferred range is about $-10$ to about $-14$ millivolts.

As noted above, as the PRC is expressed from the collection bag, it may be processed through a PRC porous medium in order to reduce the leucocyte content of the PRC. In accordance with the invention, the porous medium for removing leucocytes from the packed red cell component of whole blood comprises a device having a leucocyte removal element. The preferred element is typically made using radiation grafted melt blown fibers having an average diameter of from about 1 to about 4 μm, preferably from about 2 to about 3 μm. Polybutylene terephthalate (PBT) web, which is a preferred material, may be hot compressed to a voids volume of about 65% to about 90% and preferably to about 73% to about 88.5%.

In a preferred embodiment of the invention, a porous medium for use with packed red cells typically comprises the type of device disclosed in U.S. Pat. No. 4,925,572, herein incorporated by reference.

In packed red cells, as well as in whole blood, the red cells are suspended in blood plasma, which has a surface tension of about 73 dynes/cm. For the depletion of the leucocyte content of PRC, a CWST greater than about 53 dynes/cm is desirable. The CWST may typically be above from about 53 dynes/cm to about 115 dynes/cm, but the invention should not be limited thereby. A more preferable CWST is above about 60 dynes/cm, and a still more preferable CWST is from about 62 dynes/cm to less than about 90 dynes/cm.

The leucocyte depleting PRC filter is primarily intended for use with PRC obtained from donated blood within about 8 hours of the time the blood was drawn. It may also be used to filter PRC which has been stored at 4° C. for up to several weeks, but with the risk of clogging during filtration increasing with storage age, a risk which can be reduced, for example by using pre-filters preceding the media described herein.

A PRC porous medium of the invention can be made to have a wide range of efficiencies for leucocyte depletion. If the filter element is composed of 2.6 μm fibers and weighs about $$\rho \left( 27.98 - \frac{29.26 V}{100} \right) \text{grams} \quad (3)$$

where
$\rho$ = fiber density, grams/cc
and V = voids volume, %,
then when used for leukocyte depletion of PRC, the log of the efficiency, defined as the ratio of the influent leucocyte concentration to the effluent leucocyte concentration, may be calculated from the formula $$\text{Log efficiency} = 25.5 \left( 1 - \frac{V}{100} \right) \quad (4)$$

In most applications, it is desirable to keep the time of flow of a unit of PRC through the filter when pressurized to about 30 to 300 mm of Hg to less than about 30 to 40 minutes; in order to achieve this flow rate, the filter should preferably be configured to a flow area of about 30 to 60 cm².

For example, an 8.63 cm diameter (area=58.5 cm²) filter made using 7.7 grams of 2.6 μm diameter 1.38 g/cm³ density fiber with an element voids volume of 76.5%, would meet the requirements of equation (3), and its leucocyte depletion efficiency, in accordance with equation (4) would be log 6. Thus, if the influent concentration were 10⁹ leucocytes/unit, then the effluent concentration would be $$\frac{10^9}{10^6} = 10^3$$

Similarly, if made with V=88.2% using 2.6 μm diameter fibers of density 1.38 g/cc, the weight of the element would be, per equation (3):

$$1.38 \left[ 27.98 - \left( 29.26 \times \frac{88.2}{100} \right) \right] = 3.0 \text{ grams,}$$

and the log of the efficiency would be, per equation (4):

$$\text{Log efficiency} = 25.5 \left( 1 - \frac{88.2}{100} \right) = 3.0$$

Thus, if the influent leucocyte concentration were 10⁹ per unit of PRC, the effluent concentration would be $$\frac{10^9}{10^3} = 10^6 \text{ per unit}$$

equations (3) and (4) are applicable to a voids volume range of about 73 to 88.5%, which spans the efficiency range from about log 3 to log 7.

Equations (3) and (4) provide very useful guidelines for designing and building optimal or near to optimal PRC filters with limited experimentation; however, a person familiar with the art will recognize that variations from these formulae and modifications to the porous media can be made to produce useful products. Exemplary modifications and their effect on the performance characteristics of the filter are set out below:

| Desired Filter Characteristics | Changes from Equations (3) and (4) |
| --- | --- |
| Increased leucocyte depletion efficiency | Reduce fiber diameter[1] Increase weight of fiber Reduce voids volume |
| Decrease probability of clogging | Increase filter element area Provide prefiltration Increase voids volume |
| Decrease internal hold-up volume | Decrease voids volume[2] Eliminate prefiltration[2] Use finer fiber[1] |
| Increase flow rate of the PRC | Process the blood such that the PRC has lower hematocrit, hence lower viscosity Use higher head when filtering Increase filter area with concomitant reduction of thickness Increase filter element voids volume |
| Withstand higher applied differential pressure | Reduce element voids volume Use coarser fiber (at the cost of reduced efficiency) Use fiber with higher |

| Desired Filter Characteristics | Changes from Equations (3) and (4) |
|---|---|
| | modulus |

(1)Use of too small a fiber diameter may result in collapse of the filter element at normal working differential pressure.
(2)May result in excessively long filtration times, or complete clogging prior to completion of a transfusion.

HOUSINGS FOR POROUS MEDIA

Housings can be fabricated from any suitably impervious material, including an impervious thermoplastic material. For example, the housing may preferably be fabricated by injection molding from a transparent or translucent polymer, such as an acrylic, polystyrene, or polycarbonate resin. Not only is such a housing easily and economically fabricated, but it also allows observation of the passage of the fluid through the housing.

The housing into which the porous medium is sealed or interference fit is designed to achieve convenience of use, rapid priming, and efficient air clearance.

While the housing may be fashioned in a variety of configurations, the housing of a porous medium according to the present invention preferably comprises a housing such as that disclosed in U.S. Pat. Nos. 4,880,548; 4,923,620; and 4,925,572, which are generally similar in configuration to housing 14 in FIG. 2.

An important feature of the invention is the location and manner in which the porous medium, particularly the PRC medium, is mounted on the centrifuge bucket during the centrifugation operation. Trials of a number of test filter housings designed to fit within the centrifuge bucket convincingly demonstrated that perforation of tubing lines by the housing is a frequent occurrence during centrifugation. Also, it is very difficult to design a housing that can reliably withstand 5000G without shattering. Further, the existing centrifuge buckets are designed to carry the conventional blood collection sets, which incorporate no filter elements. Fitting the added bulk of a PRC filter assembly into a conventional bucket was, thus, very difficult. These very serious problems were eliminated by mounting the PRC filter assembly on a bracket outside of the bucket. This provides adequate support for the filter assembly by cooperatively arranging flange portion 27 of bracket 22 (FIG. 2) to accommodate the contours of the centrifuge bucket. Furthermore, bracket 22 is preferably positioned above the top of the bucket, a location which is much closer to the center of rotation of the centrifuge that the force to which the filter assembly is subjected is about 40% to about 60% that of the bottom of the bucket 20. Furthermore, the narrow slots at each end of the bracket hold the tubing connections firmly, and permit the tubes to drop back into the bowl. Surprisingly, the suspended portions of the tubing tolerate the centrifuging operation very well.

In order that the invention herein described may be more fully understood, the following examples are offered by way of illustration and not by way of limitation.

EXAMPLES

Examples 1-5

The blood collection sets used to perform the examples were in conformance with FIG. 1, and the procedure was as described earlier, using an apparatus in accordance with FIG. 2 for the first centrifuging step.

The porous medium for depleting leucocytes from PRP was preformed into a cylindrical filter element 2.5 cm in diameter and 0.33 cm thick, using PBT fibers 2.6 μm in average diameter and of density 1.38 g/cc, which had been surface modified in accordance with the procedures disclosed in U.S. Pat. No. 4,880,548, using a mixture of hydroxyethyl methacrylate and methacrylic acid monomers in a weight ratio of 0.3:1. The porous medium had a CWST of 95 dynes/cm and a zeta potential of −11.4 millivolts at the pH of plasma (7.3). Fiber surface area was 0.52 M$^2$ and voids volume was 80%.

The porous medium for depleting leucocytes from PRC, in accordance with equations (3) and (4) above, was calculated to obtain a leucocyte depletion efficiency better than log 3 (i.e. >99.9% reduction of leucocyte content). This was accomplished by using 3.4 grams of 2.6 μm diameter PBT fiber, about 13% more fiber than called for by equations (3) and (4), and, in order to further increase the leucocyte depletion efficiency, the voids volume was decreased to 81%. These changes boosted the efficiency to better than log 4 (i.e., to >99.99%). When the PRC was expressed through this filter medium contained in a housing 6.4 cm in diameter, flow times in the desired 10 to 40 minute range were obtained at 90 mm Hg applied pressure. The fiber surfaces had been modified in the manner disclosed in U.S. Pat. No. 4,925,572, using a mixture of hydroxyethyl methacrylate and methyl methacrylate in a weight ratio of 0.27 to 1; the porous medium had a CWST of 66 dynes/cm.

The PRC porous medium described above was preceded by a pre-filter consisting of five layers of PBT melt blown web laid up in the order noted below to a total thickness of 0.25 cm:

| Grade | Weight, mg/cm$^2$ | Fiber Diameter, μm | CWST |
|---|---|---|---|
| 2.0–0.6 | .002 | 12 | 50 |
| 2.0–1.0 | .002 | 9 | 50 |
| 2.5–3.5 | .003 | 4.5 | 66 |
| 5.6–7.1 | .006 | 3.0 | 66 |
| 5.2–10.3 | .006 | 2.6 | 66 |

Each of the examples used a single unit of blood donated by a volunteer. The unit of blood was collected in a blood collection set configured as shown in FIG. 1, bag 11 of the set having been pre-filled with 63 ml of CPDA anti-coagulant. The volume of blood collected from the various donors is shown in Column 1 of the Table. The collection set was positioned into the centrifuge bucket of FIG. 2 in accordance with customary blood bank practice, except that the PRC filter 14 was assembled to bracket 22, which in turn was mounted on the upper portion of the centrifuge bucket 20, thus securing PRC filter 14 outside and above the centrifuge bucket.

The centrifuge was then rotated at a speed that developed 2280G (at the bottom of the bucket) for 3 minutes, sufficient to cause the red blood cells to sediment into the lower portion of the collection bag. Bracket 22 was then removed and bag 11 was transferred, with care to avoid disturbing its contents, to a plasma extractor, which was spring biased to develop a pressure of about 90 mm Hg. Breaking the seal connecting bag 11 to PRP filter 17 and then breaking the seal connecting PRP filter 17 to bag 15 permitted the PRP supernatant layer to flow from collection bag 11 through filter 17 into satellite bag 15. As the PRP exited, the interface between the PRC and PRP rose in the collection bag 11, with flow continuing for about 10 to 20 minutes until all of the PRP had passed through filter 17, at which time the flow terminated abruptly and automatically as the leading edge of the PRC layer reached filter 17. Tubing 16 was then clamped adjacent to bag 11, and adjacent to bag 15, and the tubing between the two clamps and filter 17 was cut. The PRP collected in satellite bag 15 was then processed using normal blood bank procedures to produce leuco-depleted PC and plasma. The volumes of PC and plasma are shown in the Table along with the number of residual leucocytes in the PC.

Collection bag 11, now containing only the sedimented red cells, was removed from the plasma extractor, and 100 ml of AS3 nutrient solution, which had been preplaced in satellite bag 13, was transferred into bag 11 through filter 14. The contents of bag 11 were then thoroughly mixed. With about 120 mm Hg pressure applied by gravity head, the PRC in bag 11 was next leuco-depleted by passing it through filter 14 to bag 13. The PRC was now available for transfusion into a patient as required. The volume, hematocrits, and the residual leucocyte counts in the PRC are listed in the Table.

The leucocyte counts presented in the table reflect the sensitivity of the methods used for assaying the number of leucocytes residual in the PRC and in the PC effluents. No leucocytes were in fact detected in the leucocyte depleted effluents of any of the examples. Parallel experiments using more sensitive (but more laborious) assay methods indicate that the leucocyte depletion efficiencies were about ten to one hundred times better than is indicated by the data presented in the table.

THE TABLE

| | Test 1 | Test 2 | Test 3 | Test 4 | Test 5 |
|---|---|---|---|---|---|
| Whole Blood Collected (ml) | 407 | 387 | 399 | 410 | 410 |
| Whole Blood Hct (%) | 45 | 42.5 | 40 | 41 | 38.5 |
| PRP Filtration Time (min.) | 16 | 11 | 14 | 15 | 19 |
| PRP Volume (ml) | 211 | 173 | 196 | 177 | 232 |
| PC volume (ml) | 47 | 52 | 49 | 69 | 61 |
| Residual WBC-PC* | $<1.0 \times 10^5$ | $<1.1 \times 10^5$ | $<1.1 \times 10^5$ | $<1.5 \times 10^5$ | $<1.3 \times 10^5$ |
| PRC Filtration Time (min.) | 15 | 18 | 11 | 11 | 12 |
| PRC Volume (ml) | 285 | 318 | 301 | 306 | 288 |
| PRC Hct (%) | 64.5 | 67 | 51 | 52.5 | 60.5 |
| Residual WBC-PRC* | $<7.3 \times 10^6$ | $<8.0 \times 10^6$ | $<7.5 \times 10^6$ | $<7.7 \times 10^6$ | $<7.2 \times 10^6$ |

*per unit

While the invention has been described in some detail by way of illustration and example, it should be understood that the invention is susceptible to various modifications and alternative forms, and is not restricted to the specific embodiments set forth in the Examples. It should also be understood that these Examples are not intended to limit the invention but, on the contrary, the intention is to cover all modifications, equivalents, and alternatives falling within the spirit and scope of the invention.

What is claimed is:

1. A blood collection and processing system comprising
   a first container;
   a second container in fluid communication with the first container;
   a third container in fluid communication with the first container;
   a first porous medium interposed between the first container and the second container comprising at least one of a leucocyte depletion medium, a red cell barrier medium, and a combined leucocyte depletion red cell barrier medium; and
   a second porous medium interposed between the first container and the third container and comprising a leucocyte depletion medium.

2. The blood collection and processing system of claim 1 wherein the first container is a blood collection bag and the second and third containers are satellite bags.

3. The blood collection and processing system of claim 1 wherein the first porous medium and the second porous medium comprise fibers that have been modified by exposure to a monomer comprising a polymerizable group and a hydroxyl-containing group.

4. The blood collection and processing system of claim 3 wherein the fibers of the porous media have been modified to present hydroxyl groups and carboxyl groups.

5. The blood collection and processing system of claim 4 wherein the fibers of the first porous medium have been modified with a mixture of monomers comprising hydroxyethyl methacrylate and methacrylic acid.

6. The blood collection and processing system of claim 5 wherein the methacrylic acid to hydroxyethyl methacrylate monomer weight ratio in the modifying mixture is between 0.01:1 and 0.5:1.

7. The blood collection and processing system of claim 4 wherein the fibers of the second porous medium have been modified with a mixture of monomers comprising hydroxyethyl methacrylate and methyl acrylate or methyl methacrylate.

8. The blood collection and processing system of claim 7 wherein the methyl acrylate or methyl methacrylate to hydroxyethyl methacrylate monomer weight ratio in the modifying mixture is between 0.1:1 and 0.4:1.

9. The blood collection and processing system of claim 1 wherein the first and second porous media comprise polybutylene terephthalate fibers.

10. The blood collection and processing system of claim 1 wherein the first porous medium comprises the combined leucocyte depletion medium and a red cell barrier medium.

11. The blood collection and processing system of claim 10 wherein the first porous medium comprises a fibrous medium and wherein the fiber surface area of the first porous medium is about 0.3 to about 2.0 $M^2$.

12. The blood collection and processing system of claim 11 wherein the fiber surface area of the first porous medium is about 0.35 to about 0.6 $M^2$.

13. The blood collection and processing system of claim 11 wherein the first porous medium has a voids volume of about 75% to about 80%.

14. The blood collection and processing system of claim 10 wherein the first porous medium has a voids volume of about 71% to about 83%.

15. The blood collection and processing system of claim 10 wherein the flow of the first porous medium is about 2.5 to about 10 $cm^2$.

16. The blood collection and processing system of claim 15 wherein the flow area of the first porous medium is about 3.0 to about 6.0 $cm^2$.

17. The blood collection and processing system of claim 10 wherein the first porous medium has a zeta potential of from about $-3$ to about $-30$ millivolts at a pH of 7.3.

18. The blood collection and processing system of claim 17 wherein the first porous medium has a zeta potential of from about $-7$ to about $-20$ millivolts at a pH of 7.3.

19. The blood collection and processing system of claim 18 wherein the first porous medium has a zeta potential of from about $-10$ to about $-14$ millivolts at a pH of 7.3.

20. The blood collection and processing system of claim 10 wherein the first porous medium has a CWST of greater than about 70 dynes/cm.

21. The blood collection and processing system of claim 20 wherein the first porous medium has a CWST of about 70 dynes/cm to about 115 dynes/cm.

22. The blood collection and processing system of claim 21 wherein the first porous medium has a CWST of about 90 dynes/cm to about 100 dynes/cm.

23. The blood collection and processing system of claim 22 wherein the first porous medium has a CWST of about 93 dynes/cm to about 97 dynes/cm.

24. The blood collection and processing system of claim 10 wherein the first porous medium permits platelets to pass therethrough but blocks red blood cells.

25. The blood collection and processing system of claim 1 wherein the first porous medium comprises a fibrous medium and wherein the fiber surface area of the first porous medium is about 0.3 to about 2.0 $M^2$.

26. The blood collection and processing system of claim 1 wherein the first porous medium has a voids volume of about 71% to about 83%.

27. The blood collection and processing system of claim 1 wherein the flow area of the first porous medium is about 2.5 to about 10 $cm^2$.

28. The blood collection and processing system of claim 1 wherein the first porous medium has a zeta potential of from about 31 3 to about 31 30 millivolts at a pH of 7.3.

29. The blood collection and processing system of claim 1 wherein the first porous medium has a CWST of greater than about 70 dynes/cm.

30. The blood collection and processing system of claim 1 wherein the first porous medium permits platelets to pass therethrough but blocks red blood cells.

31. The blood collection and processing system of claim 1 wherein the first porous medium comprises a red cell barrier medium.

32. The blood collection and processing system of claim 31 wherein the first porous medium comprises a fibrous medium and wherein the fiber surface area of the first porous medium is about 0.04 to about 0.3 $M^2$.

33. The blood collection and processing system of claim 31 wherein the first porous medium has a voids volume of about 71% to about 83%.

34. The blood collection and processing system of claim 31 wherein the flow area of the first porous medium is about 3 to about 8 $cm^2$.

35. The blood collection and processing system of claim 31 wherein the first porous medium has a zeta potential of from about $-3$ to about $-30$ millivolts at a pH of 7.3.

36. The blood collection and processing system of claim 31 wherein the first porous medium has a CWST of greater than about 70 dynes/cm.

37. The blood collection and processing system of claim 1 wherein the first porous medium comprises a leucocyte depletion medium.

38. The blood collection and processing system of claim 37 wherein the first porous medium comprises a fibrous medium and wherein the fiber surface area of the first porous medium is from about 0.08 to about 1.0 $M^2$.

39. The blood collection and processing system of claim 37 wherein the first porous medium has a voids volume of about 50% to about 89%.

40. The blood collection and processing system of claim 37 wherein the first porous medium has a zeta potential of from about $-3$ to about $-30$ millivolts at a pH of 7.3.

41. The blood collection and processing system of claim 37 wherein the first porous medium has a CWST of greater than about 70 dynes/cm.

42. The blood collection and processing system of claim 1 wherein the second porous medium comprises a leucocyte depletion medium for depleting leucocytes from packed red cells.

43. The blood collection and processing system of claim 42 wherein the second porous medium has a CWST of greater than about 53 dynes/cm.

44. The blood collection and processing system of claim 43 wherein the second porous medium has a CWST of about 53 dynes/cm to about 90 dynes/cm.

45. The blood collection and processing system of claim 42 wherein the second porous medium has a voids volume of about 60% to about 90%.

46. The blood collection and processing system of claim 45 wherein the second porous medium has a voids volume of about 73% to about 88.5%.

47. The blood collection and processing system of claim 42 wherein the flow of the second porous medium is about 30 to about 60 $cm^2$.

48. The blood collection and processing system of claim 42 wherein the second porous medium also includes a pre-filter.

49. The blood collection and processing system of claim 1 wherein the second porous medium has a CWST of greater than about 53 dynes/cm.

50. The blood collection and processing system of claim 1 wherein the second porous medium has a voids volume of about 60% to about 90%.

51. The blood collection and processing system of claim 50 wherein the second porous medium has a voids volume of about 73% to about 88.5%.

52. The blood collection and processing system of claim 1 wherein the flow area of the second porous medium is about 30 to about 60 cm$^2$.

53. The blood collection and processing system of claim 1 wherein the second porous medium also includes a pre-filter.

54. The blood collection and processing system of claim 1 wherein flexible tubing connects the first container to the second container and flexible tubing connects the first container to the third container.

55. A blood collection and processing system comprising:
- a bucket;
- at least one container fitted in the bucket;
- at least one filter assembly in fluid communication with the container; and
- a bracket receiving the filter assembly and carried by the bucket.

56. The blood collection and processing system of claim 55 wherein the container is a blood collection bag.

57. The blood collection and processing system of claim 55 comprising a blood collection bag and at least one satellite bag.

58. The blood collection and processing system of claim 55 wherein the filter assembly comprises a housing and in the housing at least one of a leucocyte depletion medium, a red cell barrier medium, and a combined leucocyte depletion red cell barrier medium.

59. The blood collection and processing system of claim 55 comprising a second filter assembly in fluid communication with the container.

60. The blood collection and processing system of claim 59 wherein the second filter assembly comprises a housing and in the housing a porous medium for the depletion of leucocytes from packed red cells.

61. The blood collection and processing system of claim 59 wherein at least one filter assembly is positioned such that the force imposed on the filter assembly during centrifugation is not greater than about 60% of the force imposed at the bottom of the bucket.

62. The blood collection and processing system of claim 59 wherein at least one filter assembly is positioned outside the bucket when the filter assembly is received in the bucket and the bracket is carried by the bucket.

63. The blood collection and processing system of claim 59 wherein at least one filter assembly is positioned on the bracket and the bracket rests on or partly within the bucket.

64. The blood collection and processing system of claim 55 wherein the filter assembly is positioned such that the force imposed on the filter assembly during centrifugation is not greater than about 60% of the force imposed at the bottom of the bucket.

65. The blood collection and processing system of claim 64 wherein the force imposed on the filter assembly during centrifugation is not greater than about 40% of the force imposed at the bottom of the bucket.

66. The blood collection and processing system of claim 55 wherein the filter assembly is positioned outside the bucket when the filter assembly is received in the bucket and the bracket is carried by the bucket.

67. The blood collection and processing system of claim 55 wherein the filter assembly is positioned on the bracket and the bracket rests on or partly within the bucket.

68. A blood centrifugation and processing system comprising:
- a centrifuge having at least two buckets;
- at least one container which fits in a bucket;
- at least one filter assembly in fluid communication with the container; and
- a bracket adapted to receive the filter assembly and carried by at least one of said buckets.

69. The blood collection and processing system of claim 68 further comprising a second and a third container, wherein the first container comprises a blood collection bag and said second and third containers comprise a first and second satellite bag, respectively.

70. The blood collection and processing system of claim 68 wherein the filter assembly comprises a housing and in the housing at least one of a leucocyte depletion medium, a red cell barrier medium, and a combined leucocyte depletion red cell barrier medium.

71. The blood collection and processing system of claim 68 further comprising a second filter assembly in fluid communication with the first container.

72. The blood collection and processing system of claim 71 wherein the second filter assembly comprises a housing and a porous medium for the depletion of leucocytes from packed red cells.

73. The blood collection and processing system of claim 68 wherein the filter assembly is positioned such that the force imposed on the filter assembly during centrifugation is not greater than about 60% of the force imposed at the bottom of the bucket.

74. A blood collection and processing system comprising:
- a first container;
- a second container in fluid communication with the first container;
- a third container in fluid communication with the first container;
- a first porous fibrous medium interposed between the first container and the second container comprising at least one of a leucocyte depletion medium, a red cell barrier medium, and a combined leucocyte depletion and red cell barrier medium; and
- a second porous fibrous medium interposed between the first container and the third container and comprising a leucocyte depletion medium;
- the first and second porous media having fibers which have been modified to present hydroxyl groups.

75. The blood collection and processing system of claim 74 wherein the first container is a blood collection bag and the second and third containers are satellite bags.

76. The blood collection and processing system of claim 74 wherein the fibers of the first porous medium have been modified with a mixture of monomers comprising hydroxyethyl methacrylate and methacrylic acid.

77. The blood collection and processing system of claim 74 wherein the fibers of the second porous medium have been modified with a mixture of monomers comprising hydroxyethyl methacrylate and methyl acrylate or methyl methacrylate.

78. The blood collection and processing system of claim 74 wherein the first and second porous media comprise polybutylene terephthalate fibers.

79. The blood collection and processing system of claim 74 wherein fiber surface area in the first porous medium is about 0.3 to about 2.0 $M^2$ and the flow area is about 2.5 to about 10 $cm^2$.

80. The blood collection and processing system of claim 74 wherein the first porous medium has a voids volume of about 71% to about 83%.

81. The blood collection and processing system of claim 74 wherein the first porous medium has a zeta potential of from about $-3$ to about $-30$ millivolts at a pH of 7.3 and a CWST of greater than about 70 dynes/cm.

82. The blood collection and processing system of claim 74 wherein the second porous medium comprises a leucocyte depletion medium for depleting leucocytes from packed red cells having a CWST of greater than about 53 dynes/cm.

83. The blood collection and processing system of claim 74 wherein the second porous medium has a voids volume of about 60% to about 90% and a flow area of about 30 to about 60 $cm^2$.

84. The blood collection and processing system of claim 74 wherein the second porous medium also includes a pre-filter.

85. A blood collection and processing system comprising
- a blood collection bag;
- a first satellite bag;
- a second satellite bag;
- tubing connecting the blood collection bag to the first satellite bag and to the second satellite bag;
- a first porous medium interposed in the tubing between the collection bag and the first satellite bag comprising at least one of a leucocyte depletion medium, a red cell barrier medium, and a combined leucocyte depletion red cell barrier medium; said first porous medium having a zeta potential of about $-3$ to about $-30$ millivolts at pH of 7.3 and a CWST of greater than about 70 dynes/cm; and
- a second porous medium interposed in the tubing between the collection bag and the second satellite bag and comprising a leucocyte depletion medium, said second porous medium having a CWST of greater than about 53 dynes/cm, a voids volume of about 60% to about 90%, and a flow area of about 30 to about 60 $cm^2$.

86. A method for collecting and processing blood comprising:
- collecting whole blood in a container;
- centrifuging the whole blood;
- passing the supernatant layer of the centrifuged blood through a first porous medium, the first porous medium comprising at least one of a leucocyte depletion medium, a red cell barrier medium, and a combined leucocyte depletion red cell barrier medium; and
- passing the sediment layer of the centrifuged blood through a second porous medium, the second porous medium comprising a leucocyte depletion medium.

87. The method of claim 86 wherein centrifuging the whole blood includes separating the whole blood into a supernatant layer and a sediment layer that includes red blood cells, and wherein passing the supernatant layer through the first porous medium comprises passing the centrifuged blood, supernatant layer first, through the red cell barrier medium or the combined leucocyte depletion red cell barrier medium until the red cells block the first porous medium.

88. The method of claim 86 wherein passing the supernatant layer through a first porous medium comprises passing the layer through fibers that have been modified by exposure to a monomer comprising a hydroxyl-containing group, and wherein passing the sediment layer through a second porous medium comprises passing the layer through fibers that have been modified by exposure to a monomer comprising a hydroxyl-containing group.

89. The method of claim 86 wherein passing the supernatant layer through a first porous medium comprises passing the layer through fibers that have been modified with a mixture of monomers comprising hydroxyethyl methacrylate and methacrylic acid.

90. The method of claim 86 wherein passing the sediment layer through a second porous medium comprises passing the layer through fibers that have been modified with a mixture of monomers comprising hydroxyethyl methacrylate and methyl acrylate or methyl methacrylate.

91. The method of claim 86 wherein passing the supernatant layer through a first porous medium comprises passing the layer through polybutylene terephthalate fibers, and wherein passing the sediment layer through a second porous medium comprises passing the layer through polybutylene terephthalate fibers.

92. The method of claim 86 wherein passing the supernatant layer through a first porous medium comprises passing the layer through the combined leucocyte depletion medium and a red cell barrier medium.

93. The method of claim 86 wherein passing the supernatant layer through a first porous medium comprises passing the layer through a medium wherein the fiber surface area is about 0.3 to about 2.0 $M^2$.

94. The method of claim 86 wherein passing the supernatant layer through a first porous medium comprises passing the layer through a medium having a voids volume of about 71% to about 83%.

95. The method of claim 86 wherein passing the supernatant layer through a first porous medium comprises passing the layer through a medium having a flow area of about 2.5 to about 10 $cm^2$.

96. The method of claim 95 wherein the flow area is about 3.0 to about 6.0 $cm^2$.

97. The method of claim 86 wherein passing the supernatant layer through a first porous medium comprises passing the layer through a medium wherein the zeta potential is about $-3$ to about $-30$ millivolts at pH of 7.3.

98. The method of claim 86 wherein passing the supernatant layer through a first porous medium comprises passing the layer through a medium having a CWST of greater than about 70 dynes/cm.

99. The method of claim 86 wherein centrifuging of the whole blood comprises positioning the container containing whole blood in a centrifuge bucket and positioning a filter assembly comprising a housing and the second porous medium, on a bracket adapted to receive the filter assembly and carried by the centrifuge bucket.

100. The method of claim 99 comprising positioning the filter assembly such that the force imposed on the filter assembly during centrifugation is not greater than about 60% of the force imposed at the bottom of the centrifuge bucket.

101. The method of claim 100 comprising positioning the filter assembly such that the force imposed on the filter assembly during centrifugation is not greater than about 40% of the force imposed at the bottom of the bucket.

102. The method of claim 99 comprising positioning the filter assembly outside the bucket.

103. The method of claim 102 comprising positioning the filter assembly on a bracket which rests on or partly within the centrifuge bucket.

104. The method of claim 86 wherein passing the sediment layer through a second porous medium comprises passing the layer through a leucocyte depletion medium for depleting leucocytes from packed red cells.

105. The method of claim 86 wherein passing the sediment layer through a second porous medium comprises passing the layer through a medium having a CWST of greater than about 53 dynes/cm.

106. The method of claim 86 wherein passing the sediment layer through a second porous medium comprises passing the layer through a medium having a voids volume of about 60% to about 90%.

107. The method of claim 106 wherein passing the sediment layer through a second porous medium comprises passing the layer through a medium having a voids volume of about 73% to about 88.5%.

108. The method of claim 86 wherein passing the sediment layer through a second porous medium comprises passing the layer through a medium having a flow area of about 30 to about 60 $cm^2$.

109. The method of claim 86 wherein passing the sediment layer through a second porous medium comprises passing the layer through a medium that also includes a pre-filter.

110. The method of collecting and processing blood of claim 86 wherein the supernatant layer is passed through flexible tubing into the first porous medium, and the sediment layer is passed through flexible tubing into the second porous medium.

111. A method for collecting and processing blood comprising:
  collecting whole blood in a first container;
  centrifuging the whole blood into a supernatant component and a sediment component, wherein centrifuging the whole blood comprises positioning the first container containing the whole blood in a centrifuge bucket and positioning a filter assembly comprising a housing and a porous medium on a bracket adapted to receive the filter assembly and carried by the centrifuge bucket;
  removing the supernatant component from the first container; and
  passing the sediment component through a porous medium and into another container, wherein the porous medium removes leucocytes from packed red cells and has a CWST of greater than about 53 dynes/cm.

112. The method of claim 111 wherein positioning the filter assembly includes locating the filter assembly with regard to the bottom of the bucket such that the force imposed on the filter assembly during centrifugation is not greater than about 60% of the force imposed at the bottom of the centrifuge bucket.

113. The method of claim 112 wherein positioning the filter assembly includes locating the filter assembly with regard to the bottom of the bucket such that the force imposed on the filter assembly during centrifugation is not greater than about 40% of the force imposed at the bottom of the centrifuge bucket.

114. The method of claim 113 wherein positioning the filter assembly includes positioning the filter assembly outside the centrifuge bucket.

115. The method of claim 114 wherein positioning the filter assembly includes positioning the filter assembly on a bracket which rests on or partly within the centrifuge bucket.

116. The method of claim 111 wherein passing the sediment layer through a porous medium comprises passing the layer through a leucocyte depletion medium for depleting leucocytes from packed red cells.

117. The method of claim 111 wherein passing the sediment layer through a porous medium comprises passing the layer through a medium having a voids volume of about 60% to about 90%.

118. The method of claim 111 wherein passing the sediment layer through a porous medium comprises passing the layer through a medium having a flow area of about 30 to about 60 $cm^2$.

119. The method of claim 111 wherein passing the sediment layer through a porous medium comprises passing the layer through a medium that also includes a pre-filter.

120. A method for collecting and processing blood comprising:
  collecting whole blood in the first container of a blood collection and processing system comprising a first container for whole blood, a second container for a blood component, and a filter assembly interposed between the first container and the second container;
  placing the first container holding whole blood and the second container in a centrifuge bucket;
  positioning the filter assembly on a bracket away from the bottom of the centrifuge bucket; and
  centrifuging the system.

121. The method of claim 120 wherein positioning the filter assembly includes locating the filter assembly with regard to the bottom of the bucket such that the force imposed on the filter assembly during centrifugation is not greater than about 60% of the force imposed at the bottom of the centrifuge bucket.

122. The method of claim 120 wherein positioning the filter assembly includes positioning the filter assembly outside the centrifuge bucket.

123. The method of claim 120 wherein positioning the filter assembly includes positioning the filter assembly on a bracket which rests on the centrifuge bucket.

* * * * *

UNITED STATES PATENT AND TRADEMARK OFFICE
CERTIFICATE OF CORRECTION

PATENT NO. : 5,100,564

DATED : March 31, 1992

INVENTOR(S) : PALL ET AL.

It is certified that error appears in the above-identified patent and that said Letters Patent is hereby corrected as shown below:

Claim 28, column 21, line 61, change "31 3" to -- -3--;
change "31 30" to -- -30--.

Signed and Sealed this

Seventh Day of December, 1993

Attest:

BRUCE LEHMAN

*Attesting Officer*  *Commissioner of Patents and Trademarks*